US010588491B2

(12) United States Patent
Ponsky

(10) Patent No.: US 10,588,491 B2
(45) Date of Patent: Mar. 17, 2020

(54) ACCESSORY MEDICAL DEVICE INTRODUCTION APPARATUS FOR ENDOSCOPES

(71) Applicant: University Hospitals Health System, Inc., Cleveland, OH (US)

(72) Inventor: Lee Ponsky, Moreland Hills, OH (US)

(73) Assignee: University Hospitals Health System, Inc., Cleveland, OH (US)

( * ) Notice: Subject to any disclaimer, the term of this patent is extended or adjusted under 35 U.S.C. 154(b) by 333 days.

(21) Appl. No.: 15/535,611

(22) PCT Filed: Dec. 10, 2015

(86) PCT No.: PCT/US2015/064919
§ 371 (c)(1),
(2) Date: Jun. 13, 2017

(87) PCT Pub. No.: WO2016/100072
PCT Pub. Date: Jun. 23, 2016

(65) Prior Publication Data
US 2017/0360281 A1    Dec. 21, 2017

Related U.S. Application Data

(60) Provisional application No. 62/094,448, filed on Dec. 19, 2014.

(51) Int. Cl.
*A61B 1/00* (2006.01)
*A61B 1/018* (2006.01)
(52) U.S. Cl.
CPC .......... *A61B 1/00135* (2013.01); *A61B 1/018* (2013.01)

(58) Field of Classification Search
USPC .......................................................... 600/114
See application file for complete search history.

(56) References Cited

U.S. PATENT DOCUMENTS 4,211,234 A * 7/1980 Fisher ............... A61M 16/0488
128/200.26
4,601,713 A * 7/1986 Fuqua ............... A61M 25/0023
604/103.14

(Continued)

OTHER PUBLICATIONS

International Search Report and Written Opinion for International Application No. PCT/US2015/064919, dated Apr. 1, 2016.

*Primary Examiner* — Timothy J Neal
*Assistant Examiner* — Jae Woo
(74) *Attorney, Agent, or Firm* — Renner, Otto, Boisselle & Sklar, LLP

(57) ABSTRACT

An accessory device introduction system works in conjunction with an endoscope and enables more than one accessory device to be used at the same time. The system has a plurality of channels which only expand to accommodate said accessory device(s) when introduced. The system further includes an attachment assembly which connects securely to the endoscope by means of a compression friction fit between the endoscope and itself. The attachment assembly also provides at least one accessory port to be presented to an end user to enable the end user to pass an accessory device within said accessory port and channel. The system further includes a multi-channeled endoscope shaft sheath which is connected to the attachment assembly at one end and the distal end of the endoscope shaft at the other end, thereby covering an entire outer shaft diameter length. The shaft sheath has a plurality of channels which correspond to those of the attachment assembly.

18 Claims, 11 Drawing Sheets

(56) References Cited

U.S. PATENT DOCUMENTS

| | | | | |
|---|---|---|---|---|
| 4,748,969 A * | 6/1988 | Wardle | A61B 1/0051 | 138/120 |
| 4,798,193 A * | 1/1989 | Giesy | A61M 25/0105 | 600/114 |
| 5,025,778 A * | 6/1991 | Silverstein | A61B 1/0008 | 600/104 |
| 5,106,368 A * | 4/1992 | Uldall | A61M 25/003 | 604/178 |
| 5,217,001 A * | 6/1993 | Nakao | A61B 1/00135 | 24/DIG. 50 |
| 5,259,366 A * | 11/1993 | Reydel | A61B 1/00135 | 383/203 |
| 5,334,167 A * | 8/1994 | Cocanower | A61J 15/0003 | 604/172 |
| 5,353,783 A * | 10/1994 | Nakao | A61B 1/00135 | 600/106 |
| 5,483,951 A * | 1/1996 | Frassica | A61B 1/00142 | 600/104 |
| 5,503,616 A * | 4/1996 | Jones | A61B 1/00135 | 600/121 |
| 5,573,508 A * | 11/1996 | Thornton | A61M 25/104 | 604/102.02 |
| 5,749,889 A * | 5/1998 | Bacich | A61B 17/3417 | 600/104 |
| 5,772,628 A * | 6/1998 | Bacich | A61B 17/3417 | 604/43 |
| 5,810,776 A * | 9/1998 | Bacich | A61B 17/3417 | 604/131 |
| 5,827,177 A * | 10/1998 | Oneda | A61B 1/00071 | 600/121 |
| 6,293,909 B1 * | 9/2001 | Chu | A61B 1/00071 | 600/121 |
| 6,695,772 B1 * | 2/2004 | Bon | A61B 17/3421 | 600/114 |
| 7,347,853 B2 * | 3/2008 | DiFiore | A61M 25/0075 | 604/256 |
| 7,875,019 B2 * | 1/2011 | Barron | A61M 25/0014 | 604/534 |
| 2002/0032370 A1 * | 3/2002 | Kamata | A61B 1/018 | 600/140 |
| 2007/0142709 A1 * | 6/2007 | Martone | A61B 1/00135 | 600/121 |
| 2011/0092766 A1 * | 4/2011 | Monassevitch | A61B 1/0008 | 600/104 |
| 2013/0261390 A1 * | 10/2013 | Hirsch | A61B 1/00135 | 600/114 |
| 2015/0173589 A1 * | 6/2015 | Mitchell | A61B 1/0052 | 600/142 |
| 2019/0151587 A1 * | 5/2019 | Vazales | A61M 16/0463 | |

* cited by examiner

ACCESSORY MEDICAL DEVICE INTRODUCTION APPARATUS FOR ENDOSCOPES

RELATED APPLICATIONS

This application is a national phase of International Patent Application Ser. No. PCT/US2015/064919 filed on Dec. 10, 2015 which claims the benefit of U.S. Provisional Application No. 62/094,448 filed Dec. 19, 2014, both of which are incorporated herein by reference.

FIELD OF INVENTION

The present invention relates generally to medical endoscopes, and more particularly to components, systems, and method for medical device introduction using endoscopes.

BACKGROUND

Endoscopes are presently used for diagnostic and therapeutic purposes. There are many different uses for endoscopes, and frequently the endoscope design is varied, depending on its use, to optimize the performance of the endoscope for its intended purpose. As such, there are specific endoscopes for the areas in which they are used. For example, there are upper endoscopes for examination of the esophagus, stomach and duodenum, bronchoscopes for examining the bronchi, laparoscopes for examining the peritoneal cavity, arthroscopes for examining joint spaces, angioscopes for examining the blood vessels and heart, colonoscopes for examining the colon, sigmoidoscopes for examining the rectum and sigmoid colon, and cystoscopes for examining the urethra and bladder.

The endoscope may include one or more diagnostic or treatment devices, such as tubings for water, air and biopsy suction; a viewing device, a temperature sensor, a heating probe, an ultrasonic sensor, a laser catheter or the like. The tubings inside the endoscope must be capable of bending or flexing without kinking or collapsing as the endoscope is moved through the body.

In the field of endoscopes, a conventional endoscope 5, shown in FIG. 1, has an insertion tube 17 connected at its proximal end 19 to a handle or control body 20. The insertion tube 17 is adapted to be inserted into a patient's body cavity to perform a selected therapeutic or diagnostic procedure. The insertion tube 17 contains an imaging system having optical fibers or the like extending along the length of the insertion tube and terminating at a viewing window 22 in the insertion tube's distal end 18. The imaging system conveys an image from the viewing window 22 to an eyepiece 23 on the control body 20 or to a monitor (not shown), so the user can see into a selected body cavity during an endoscopic procedure. The endoscope 5 is described in greater detail in U.S. Pat. No. Re 34,110 and U.S. Pat. No. 4,646,722, which are incorporated herein by reference.

Endoscopes are limited in utilising additional equipment by the number and diameter of the working channels in which it incorporates.

Cystoscopy is endoscopy of the urinary bladder via the urethra. It is carried out with a cystoscope. The urethra is the tube that carries urine from the bladder to the outside of the body. The cystoscope has lenses like a telescope or microscope. These lenses let the physician focus on the inner surfaces of the urinary tract. Some cystoscopes use optical fibres (flexible glass fibres) that carry an image from the tip of the instrument to a viewing piece at the other end. Cystoscopes range from paediatric to adult and from the thickness of a pencil up to approximately 9 mm and have a light at the tip. Many cystoscopes have extra tubes to guide other instruments for surgical procedures to treat urinary problems.

There are two main types of cystoscopy, flexible and rigid, differing in the flexibility of the cystoscope. Flexible cystoscopy is carried out with local anaesthesia on both sexes, typically with a topical anaesthetic. Rigid cystoscopy can be performed under the same conditions, but is generally carried out under general anaesthesia, particularly in male subjects, due to the pain caused by the probe.

One of the complications requiring observation and treatment within the urinary tract is the occurrence of kidney stones. A kidney stone, also known as a renal calculus (from the Latin rēnēs, "kidneys", and calculus "pebble"), is a solid concretion or crystal aggregation formed in the kidneys from dietary minerals in the urine.

Urinary stones are typically classified by their location in the kidney (nephrolithiasis), ureter (ureterolithiasis), or bladder (cystolithiasis), or by their chemical composition (calcium-containing, struvite, uric acid, or other compounds). About 80% of those with kidney stones are men.

Kidney stones typically leave the body by passage in the urine stream, and many stones are formed and passed without causing symptoms. If stones grow to sufficient size (usually at least 3 millimeters (0.12 in)) they can cause obstruction of the ureter. Ureteral obstruction causes postrenal azotemia and hydronephrosis (distension and dilation of the renal pelvis and calyces), as well as spasm of the ureter. This leads to pain, most commonly felt in the flank (the area between the ribs and hip), lower abdomen, and groin (a condition called renal colic). Renal colic can be associated with nausea, vomiting, fever, blood in the urine, pus in the urine, and painful urination. The diagnosis of kidney stones is made on the basis of information obtained from the history, physical examination, urinalysis, and radiographic studies. Ultrasound examination and blood tests may also aid in the diagnosis.

When a stone causes no symptoms, watchful waiting is a valid option. For symptomatic stones, pain control is usually the first measure, using medications such as nonsteroidal anti-inflammatory drugs or opioids. More severe cases may require surgical intervention. For example, some stones can be shattered into smaller fragments using extracorporeal shock wave lithotripsy. Some cases require more invasive forms of surgery. Examples of these are cystoscopic procedures such as laser lithotripsy or percutaneous techniques such as percutaneous nephrolithotomy. Sometimes, a tube (ureteral stent) may be placed in the ureter to bypass the obstruction and alleviate the symptoms, as well as to prevent ureteral stricture after ureteroscopic stone removal.

Currently, if a patient presents with a kidney stone and requires a stent to be placed in their ureter, they must be sent for a rigid cystoscopy which involves general anesthetic with associated risks and costs. Flexible cystoscopes allow ureter visualization and access via guide wire, but minimal working channel diameter prevents stent placement and the relieving of patient discomfort.

Endoscopes must be adequately cleaned and sterilized between each use to ensure that disease is not transmitted from one patient to another. For example, upper endoscopes, colonoscopes, angioscopes and sigmoidoscopes all come in contact with the blood and other body fluids which are capable of transmitting diseases from one person to another. Even though the endoscopes are cleaned between each use, often using chemicals, such as glutaraldehyde, complete sterilization is not ensured. Some body particles may lodge in a crevice of the endoscope and not be contacted by the sterilization fluid.

Optimization of intrabody medical equipment for such therapeutic and diagnostic procedures has resulted in sterile, inexpensive disposable components that are used alone or with non-disposable equipment.

There are many examples of disposable endoscopic sheath assemblies currently in common use today and variations of the process described in the above paragraphs are commonly used and are well known in the prior art. The substantial prior art in this area can be referenced in the cited patents of this document.

Disposable endoscopic sheath assemblies are primarily used to cover the endoscope insertion tube and protect it from contaminating a patient during use. Accordingly, the sheath assemblies alleviate the problem and cost of cleaning and sterilizing the insertion tube between endoscopic procedures. The sheaths and endoscopes are usable in medical applications and also in industrial applications, such as visually inspecting difficult to reach areas in an environment that could damage or contaminate the endoscope.

The sheath can be made from an inelastic polymer, such as PVC, acrylic, polycarbonate, polyethylene terephthalate or other thermoplastic polyesters, or can be made from an elastomeric material. Both materials presently have advantages and disadvantages. Inelastic materials allow for thin-walled medical components that exhibit high strength and visible clarity. Using inelastic materials, the sheath can be formed with a thin wall (measuring 0.003 inches or less).

Inelastic materials, however, have a number of disadvantages. Tight-fitting sheaths formed from inelastic materials may overly restrict bending when used with flexible insertion tubes. The insertion tube combined with the tight-fitting, inelastic sheath can only bend over a limited radius. If bent further, the sheath will either buckle, in the case of a thick-walled sheath, or the sheath material will become taught, in the cause of a thin-walled sheath, preventing the insertion tube from bending further. Consequently, if the inelastic sheath is to be used in combination with a flexible endoscope, the sheath is typically either baggy or must contain bending features, such as accordion-like baffles or the like, to allow the insertion tube to sufficiently bend. Both baggy sheaths and these additional bending features add to the cross-sectional size of the sheath during use, which may result in additional pain or discomfort to the patient.

Conventional elastic sheaths have been developed and used with imaging devices such as endoscopes to overcome the drawbacks associated with the inelastic sheaths described above and to provide additional benefits. As an example, conventional elastic sheaths are designed so the sheath will easily bend with the insertion tube without substantially affecting the insertion tube's bending characteristics. The elastic sheath can be designed to closely or tightly cover the insertions tube while still being able to bend with the insertion tube, so the elastic sheath does not need additional bending features.

Elastic materials, however, also have some disadvantages. First, conventional elastic sheaths are manufactured by extruding elastomeric material. The extruded elastic sheaths, however, have manufacturing limits that restrict the minimum wall thickness of the sheath, particularly for sheaths having small internal diameter. Efforts toward manufacturing such a sheath have typically resulted in the extruded material collapsing or wrinkling and adhering to itself during the process. As a result, the extruded elastic sheath must be made with a relative thick wall (i.e., greater than 0.006 inches). The thicker the sheath wall, in a tight-fitting sheath, the greater the resistance to bending.

Tight fitting, elastic sheaths can also be complex and expensive to install onto the insertion tube. The elastic materials commonly used to manufacture the sheath have high friction characteristics. As a result, it can be difficult to insert the insertion tube into the tight-fitting sheath because the insertion tube binds on the inner wall of the sheath. One solution is to make the sheath with a diameter considerably larger than the insertion tube, so the sheath is baggy when installed on the insertion tube. Baggy sheaths, however, are undesirable in many endoscopic procedures because the sheath can be twisted, bunched, or misaligned relative to the insertion tube during the procedure. The baggy sheath can also increase the diameter of the sheathed insertion tube, which can increase pain or discomfort to the patient.

In the design of intra-body medical devices and accessories, including optical and non-optical devices, there is a need for components having the benefits of both elastic and inelastic materials while, at the same time, avoiding the disadvantages associated with these materials. As an example, there is a need for an elastic component that can be manufactured with both a thin wall and a small internal diameter. There is also a need for a small diameter, elastic sheath that can be quickly and inexpensively installed and used on a flexible insertion tube. Other medical devices and accessories would also benefit by such inexpensive, elastic, thin-walled components.

Presently, a limiting constraint in designing endoscopes is that the diameter of the endoscope must be less than the diameter of the body cavity through which the endoscope must travel. And the ability of a patient to tolerate an endoscope is related to its diameter. An endoscope for use in the stomach cannot be larger in diameter than the esophagus. Endoscopes for use in the gastrointestinal tract cannot be larger in diameter than the rectum, colon or large intestine, depending upon the length which the endoscope is inserted into the digestive tract. Angioscopes for examining the blood vessels and heart must be smaller in diameter than the smallest blood vessel through which the angioscope must pass.

The medical diagnostic and treatment which can be performed using an endoscope may be limited by its diameter. For example, the diameter of the endoscope may not be sufficiently large to permit both an ultrasonic probe and a video probe to be located within the same endoscope. Similarly, the physician may desire to have an endoscope which includes a video probe, a biopsy channel and graspers for removing tissue viewed by the video probe. However, the diameter of the endoscope may be limited to a size smaller than that required to include a grasper, a biopsy channel and a video probe in the same endoscope. The physician may wish to have a temperature sensor, heater probe, multiple-arm grasper, wash channel, forward viewing video probe, side viewing video probe, binocular lens, wide angle lens, ultrasonic sensors, ultrasonic heating devices, lasers, micrometers or the like for use alone or in combination with each other in diagnosing or treating a patient. Unfortunately, the diameter of the body cavity through which the endoscope must pass may not be sufficiently large to permit an endoscope to be routinely passed which is sufficiently large to accommodate more than one or two of the possible diagnostic and treatment devices which might need to be used.

SUMMARY OF INVENTION

The present invention embodies a disposable sheath assembly fitted over a flexible endoscope insertion tube that contains radially expandable side rails, to open a working channel and provide the means to introduce and place additional accessories.

An expandable channel would also allow the future development of more advanced devices to be developed for flexible endoscopy.

An accessory device introduction system works in conjunction with an endoscope and enables more than one accessory device to be used at the same time. The accessory device introduction system has a plurality of channels which only expand to accommodate said accessory device(s) when introduced. The accessory device introduction system further includes an attachment assembly which connects securely to the endoscope by means of a compression friction fit between the endoscope and itself. The attachment assembly also provides at least one accessory port to be presented to an end user to enable the end user to pass an accessory device within said accessory port and channel. The accessory device introduction system further includes a multi-channeled endoscope shaft sheath which is connected to the attachment assembly at one end and the distal end of the endoscope shaft at the other end, thereby covering an entire outer shaft diameter length. The endoscope shaft sheath has a plurality of channels which correspond to those of the attachment assembly.

The foregoing and other features of the invention are hereinafter described in greater detail with reference to the accompanying drawings.

DETAILED DESCRIPTION

Figure 1:
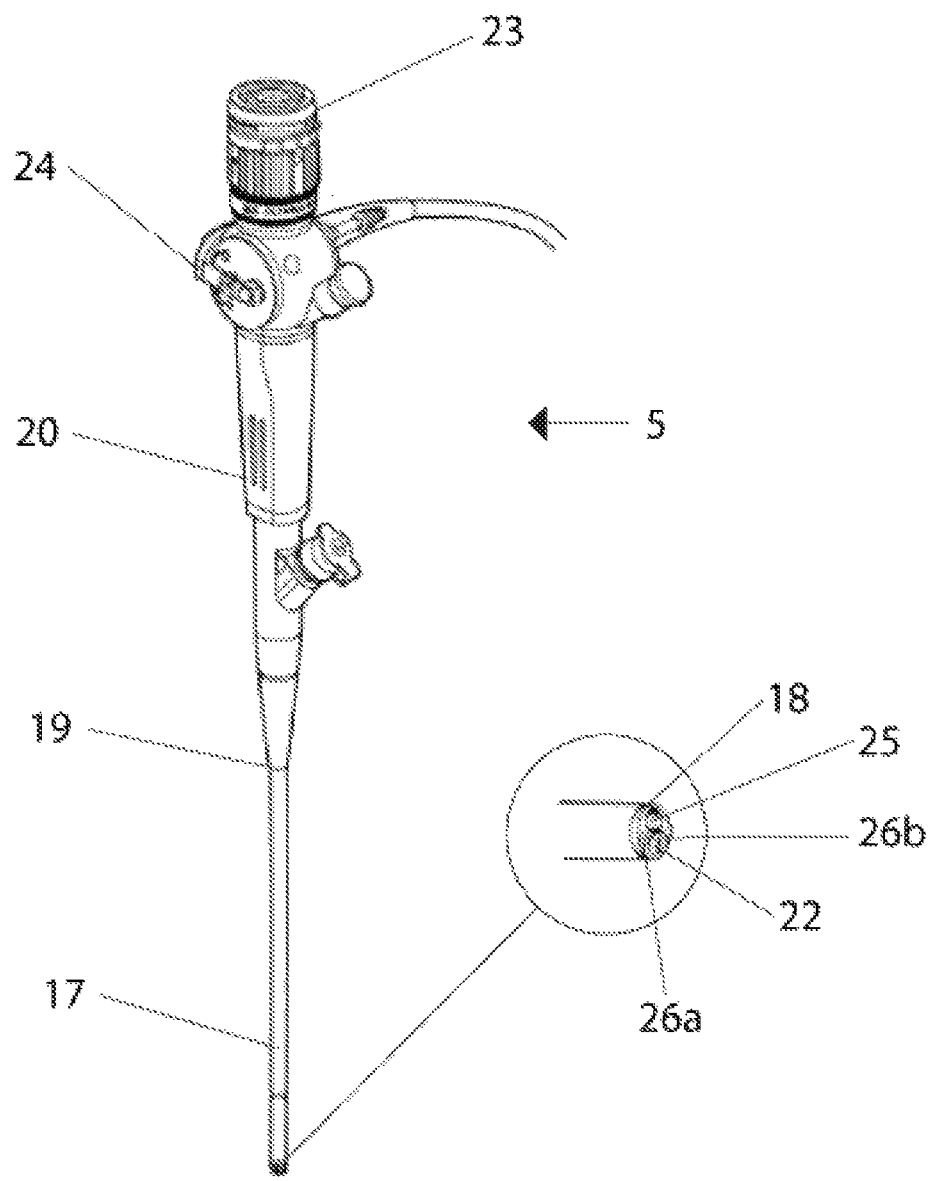
FIG. 1 is a drawing depicting an exemplary endoscope design.
Figure 2:
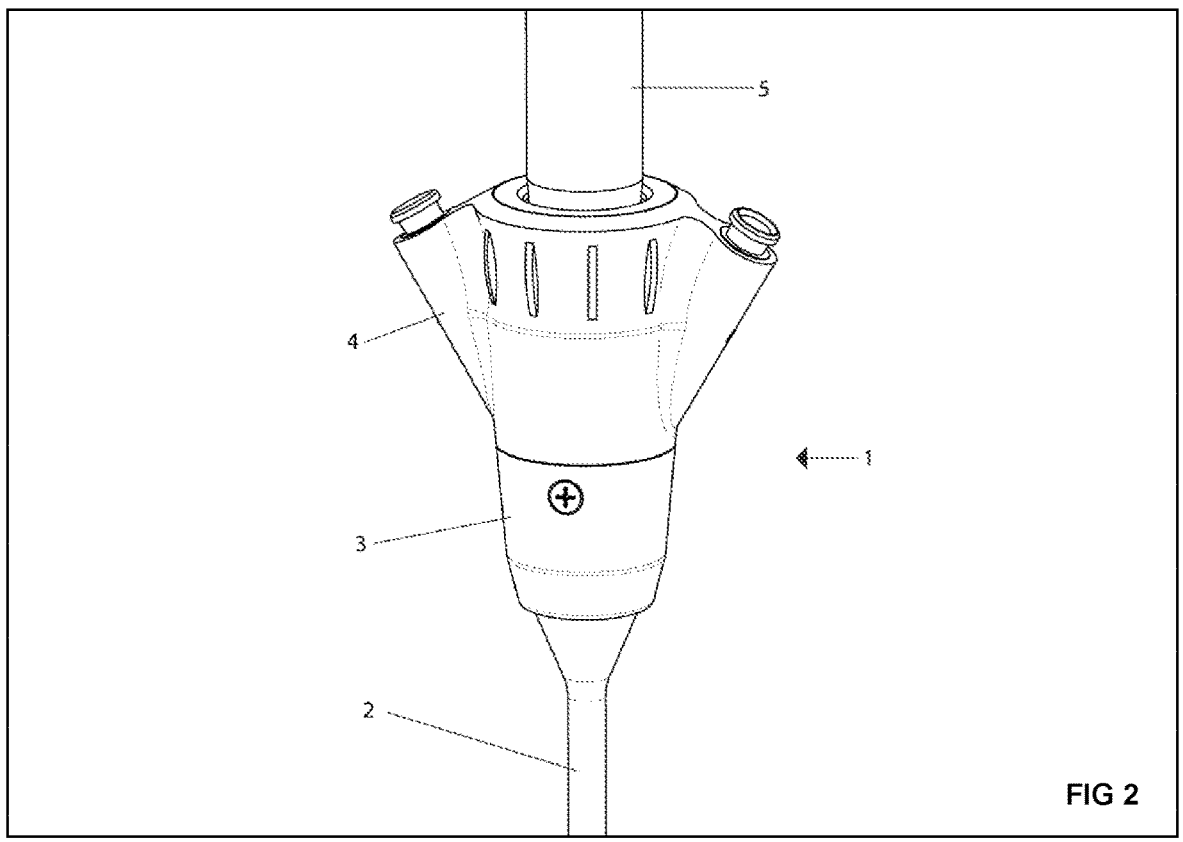
FIG. 2 is a drawing depicting another exemplary endoscope design in accordance with embodiments of the present invention.

[FIGS. 1 & 2] The present detailed description describes an apparatus 1 and method for providing an endoscope 5 with a plurality of potential channels. A sheath assembly 2, having a radially flexible wall, is positioned over an endoscope insertion tube 17. After insertion of the insertion tube 17 into the patient's body, the sheath assembly 2 is expanded to create a channel by feeding a wire-guide or medical accessory into said sheath assembly 2. A medical accessory may pass through the channel for performing a medical procedure. By expanding the flexible sheath, medical accessories are permitted to extend from a position outside of the patient's body to the distal end of the insertion tube. A plurality of channels are provided circumferentially spaced around the insertion tube to permit a combination of medical accessories to be used in co-operation with each other to perform a medical procedure.

Figure 3:
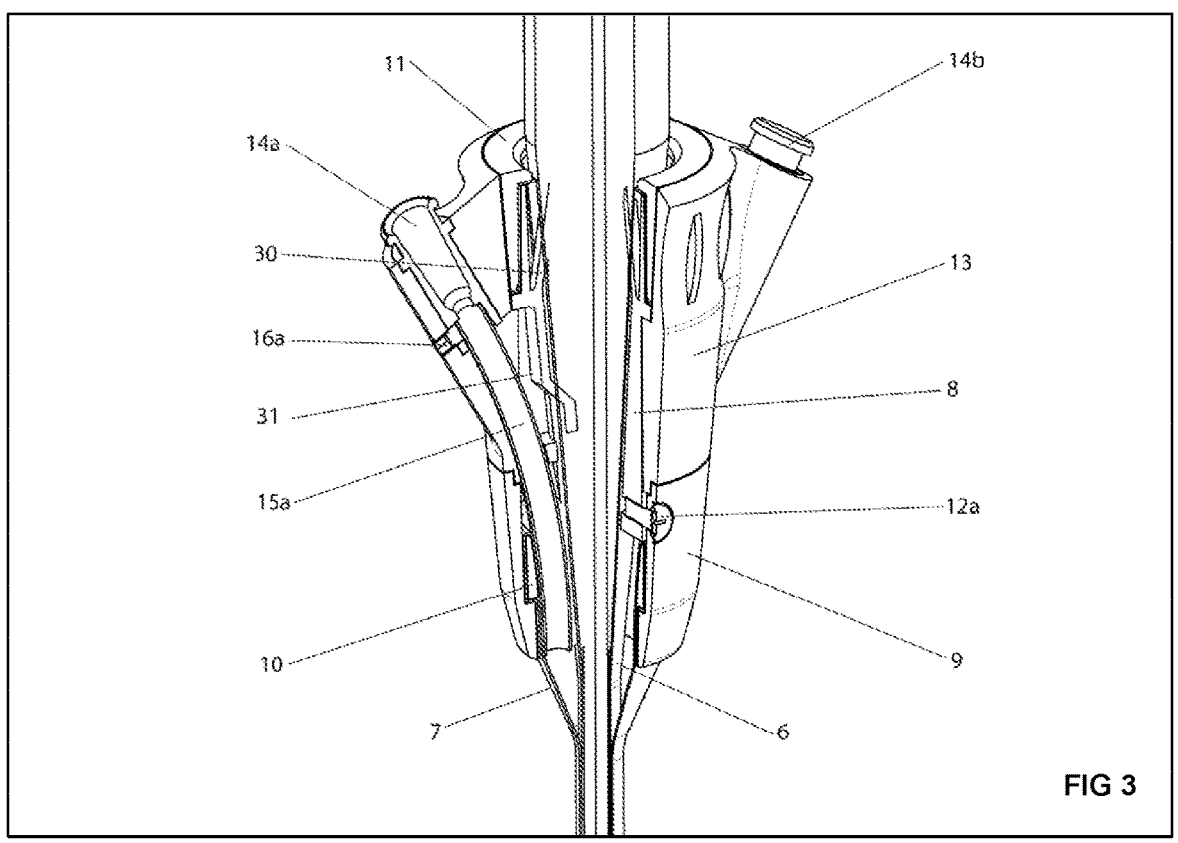
FIG. 3 is a drawing depicting the configuration of internal components of the endoscope of FIG. 2.
Figure 4:
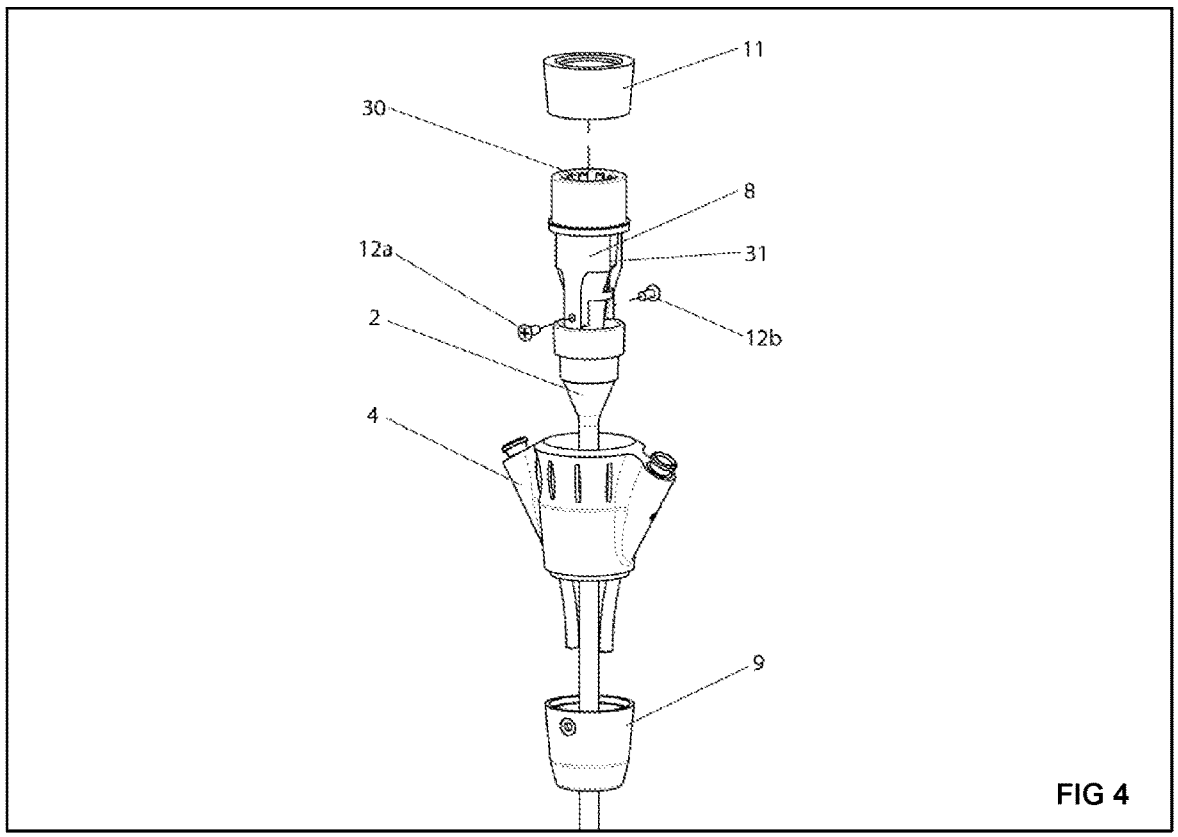
FIG. 4 is a drawing depicting an exploded view of an exemplary endoscope in accordance with embodiments of the present invention.
Figure 5:
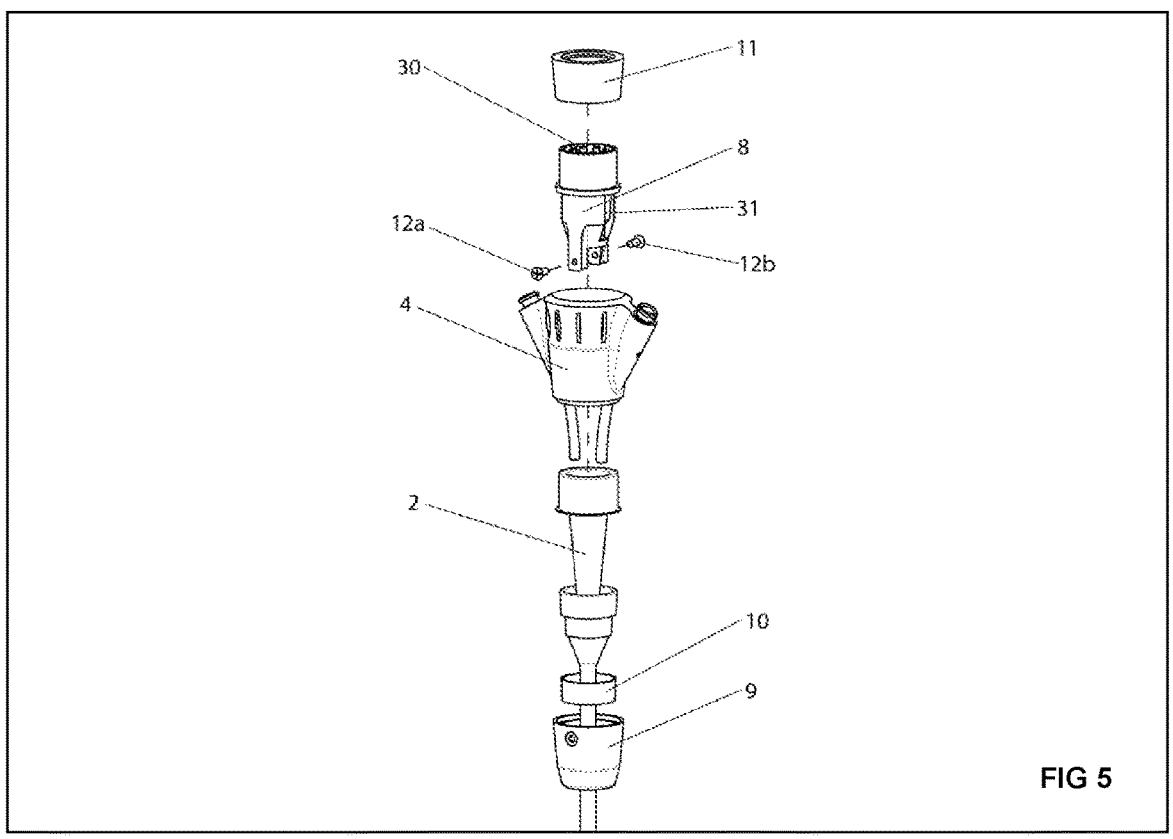
FIG. 5 is a drawing depicting an exploded view of another exemplary endoscope in accordance with embodiments of the present invention.

[FIGS. 1, 2 & 3] The present invention relates to an apparatus 1 which is inserted over the insertion tube 17 of an endoscope 5, wherein, said apparatus 1 is used to provide one or more access ports 14 (e.g., ports 14a and 14b) for delivering secondary endoscopic devices to the distal tip 18 of an endoscope 5 outside of the scope of pre-existing defined working channels.

Secondary accessories could be, but are not limited to; guide-wires, introduction tubes, stents, grabbers, snippers or any other endoscopic device.

[FIGS. 1-5 & 11] Embodiments of the current invention relate to the configuration and construction of the inner and outer sheath of the sheath assembly 2 over the endoscope insertion tube 17 such that the expansion of said portions of the sheath assembly 2 creates one or more self-contained working channels 27.

The apparatus 1 is of a length such that it will be positioned securely on the initial handle taper 20 of the longest currently available endoscope 5 and lower down, but still securely on the shortest length endoscope 5 currently available.

[FIGS. 1-5 & 11] The present invention relates to an apparatus that can be fitted onto an endoscope over its insertion tube 17, wherein said apparatus comprises a fixed portion 3 that affixes to the initial portion of an endoscope control handle 20, a rotating portion 4 that provides accessory device access and a sheath assembly 2 that encapsulates the endoscope insertion tube 17 and provides one or more working channels 27 that extend along the insertion tube 17 and are adapted to receive conventional endoscopic accessories there-through.

[FIGS. 1, 2 & 3] In the current embodiment, the fixed portion 3 of the apparatus retains the sheath assembly 2 and provides an internal coupling designed to expand to accommodate and provide a friction fit onto the initial tapered handle section 20 of a range of endoscope 5 diameters. This is achieved by a number of spring fingers 30 & 31, incorporated in the fixed part 8 construction, that flex outwards adjusting to the diameter of the endoscope handle 20 it is fitting to. Alternate methods for affixing to an endoscope handle 20 include O-ring seals or olive compression seals.

Figure 7:
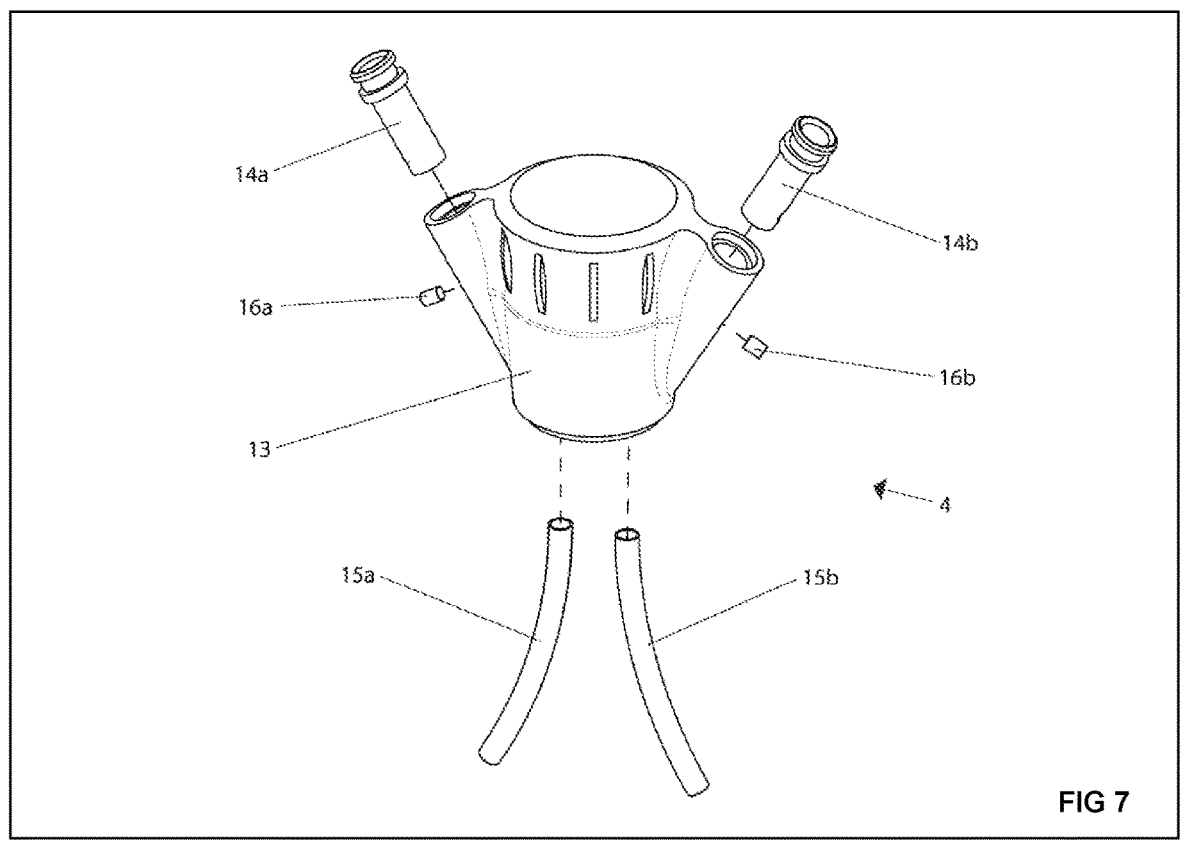
FIG. 7 is a drawing depicting an exploded view of an exemplary rotating portion of an endoscope.

[FIGS. 3 & 7] The rotating portion 4 of the apparatus 1 incorporates one or more access ports 14 and in conjunction a similar number of access funnels 15 in order to provide a smooth path for the introduction of accessories from external to the apparatus and deliver them to a position between the inner and outer sheaths of the sheath assembly 2. The rotating portion 4 has a range of motion to rotate around a central axis of the fixed portion 3, which is a novel aspect, providing adjustability of accessory introduction feeding.

[FIG. 3] The access funnels 15 extend into the gap between the inner sheath 6 and an outer sheath 7 of the sheath assembly 2 to ensure continuation of feed path.

[FIG. 3] The transition between access port 14 and access funnel 15 is designed to be seamless to ensure the smooth introduction of accessory devices.

Figure 6:
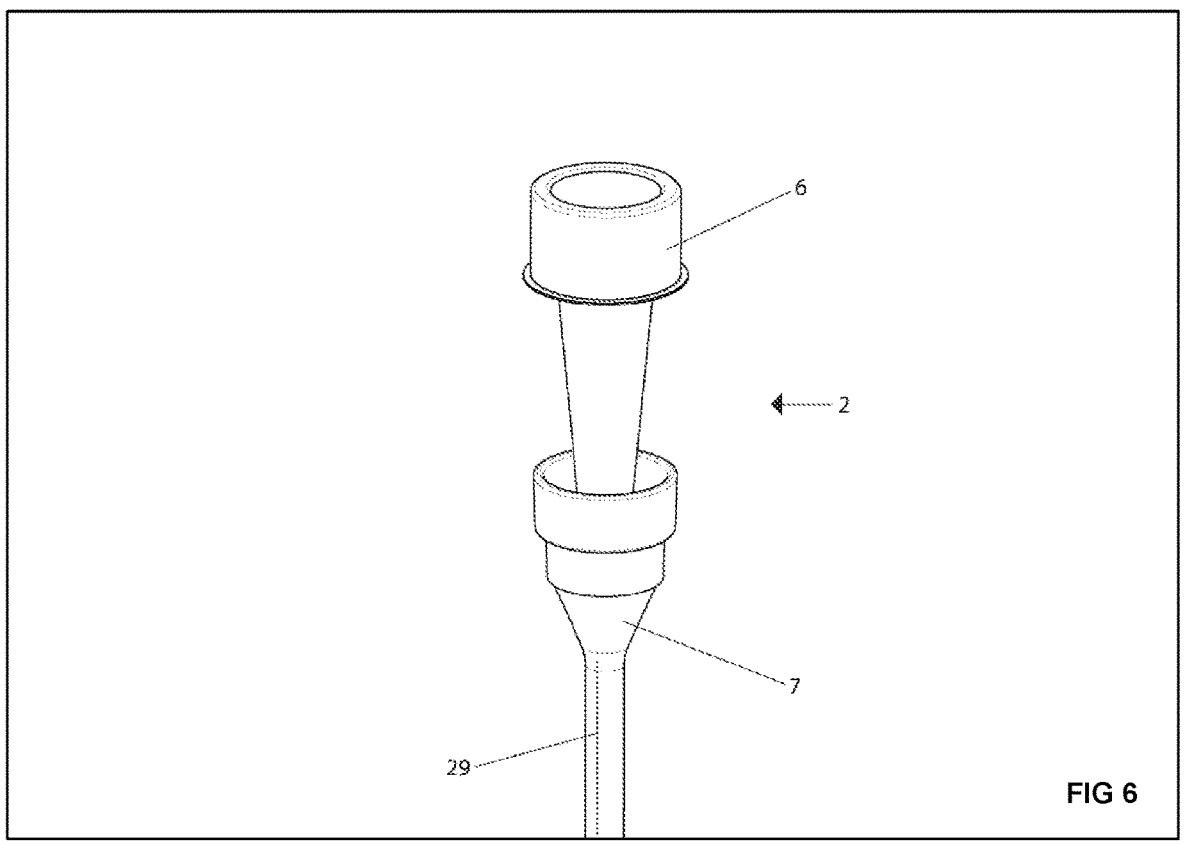
FIG. 6 is a drawing depicting a partially exploded view of an exemplary sheath portion of an endoscope.

[FIGS. 3 & 6] The fitted sheath assembly 2 is comprised of two layers of differing materials, joined longitudinally to comprise a single entity, and provide one or more working channels between the two materials.

[FIG. 6] The sheath assembly 2 includes an inner sheath 6 that is made of a sufficiently non-elastic material to prevent axial stretch and with lubricious outer face to aid accessory device insertion.

[FIG. 6] The sheath assembly 2 further includes an outer sheath 7 that is made of an elastic material chosen for its ability to stretch in a horizontal radial direction but is restricted in stretch in the longitudinal direction. A 2-way weft knit fabric would be preferable but could be from a material containing a percentage composition of Spandex/Lycra that achieves this functionality.

Figure 8:
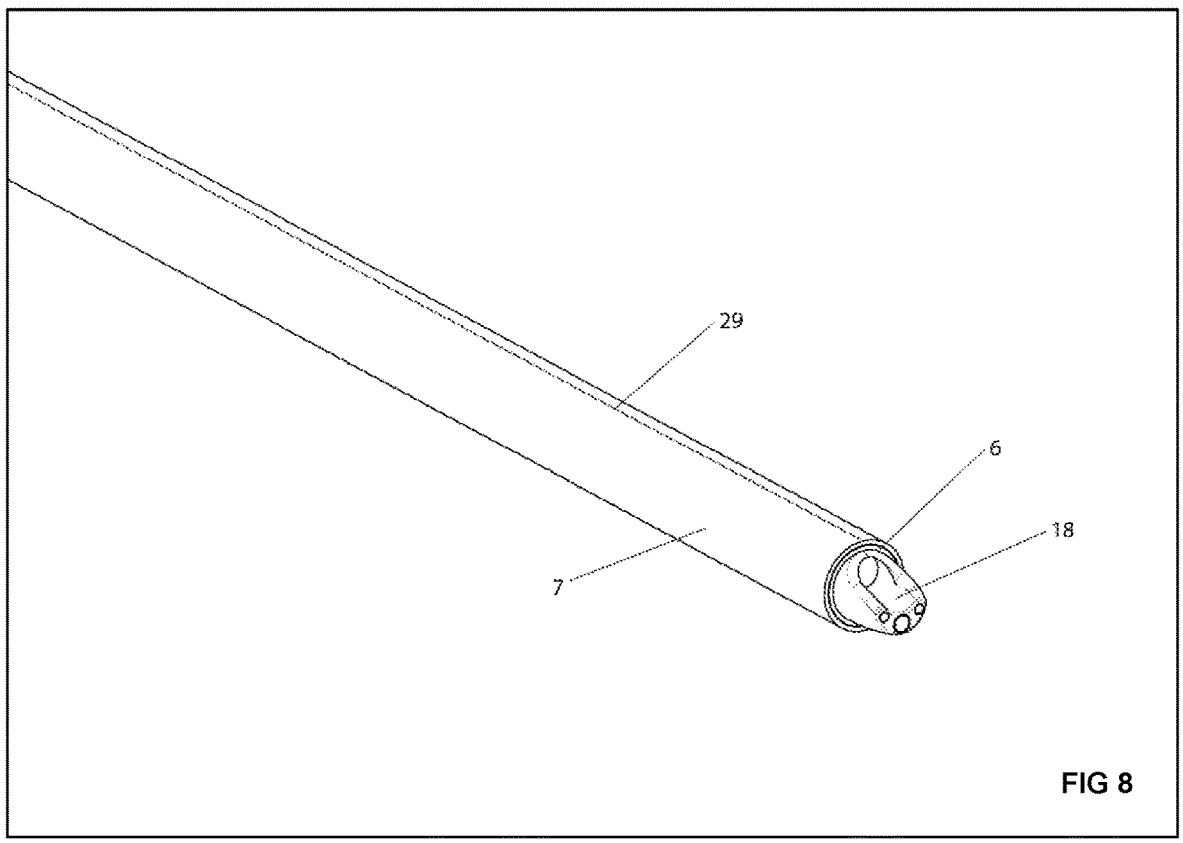
FIG. 8 is a drawing depicting an exemplary rotating inner sheath component of an endoscope.
Figure 9:
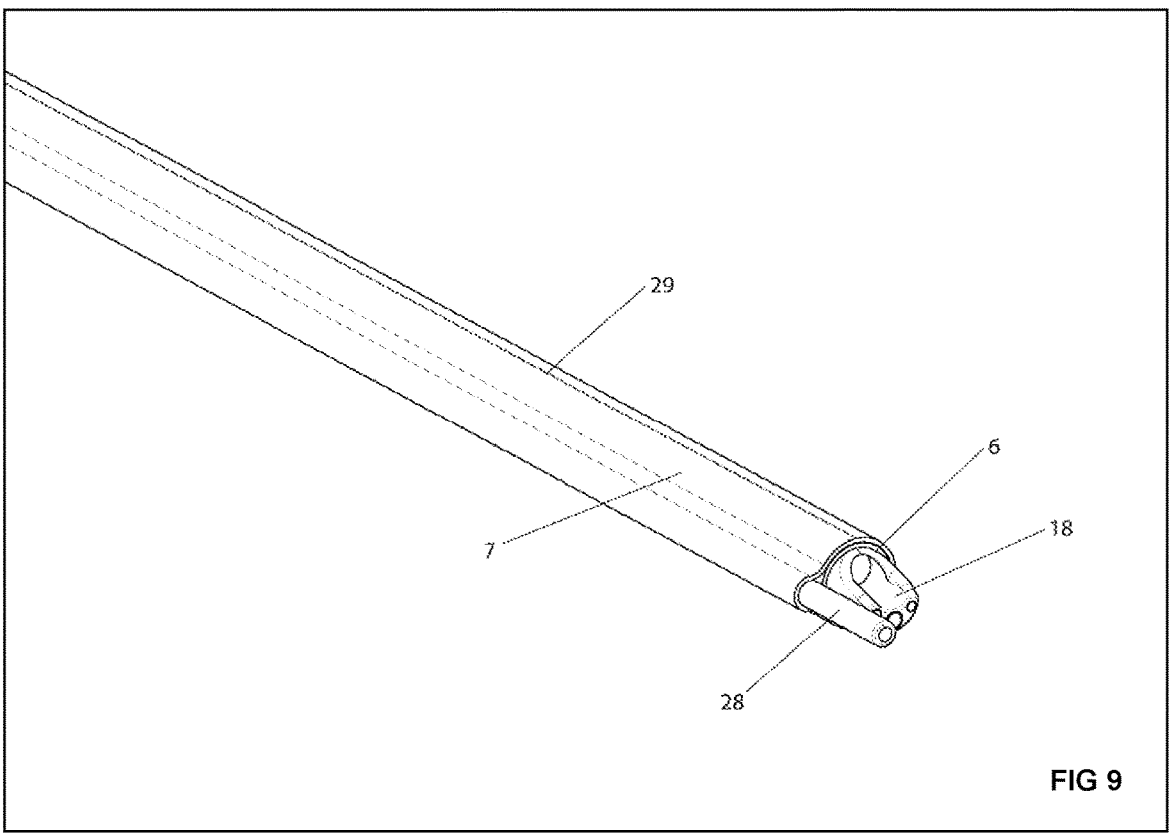
FIG. 9 is a drawing depicting the exemplary rotating inner sheath component of an enodscope of FIG. 8, in combination with a secondary accessory.

[FIG. 8] The inner sheath 6 of the conjoined sheath assembly 2 tapers in circumference at the distal tip to provide a fitted grip onto the endoscope atraumatic insertion tip 18 preventing the endoscope insertion tube 17 from passing through.

Figure 10:
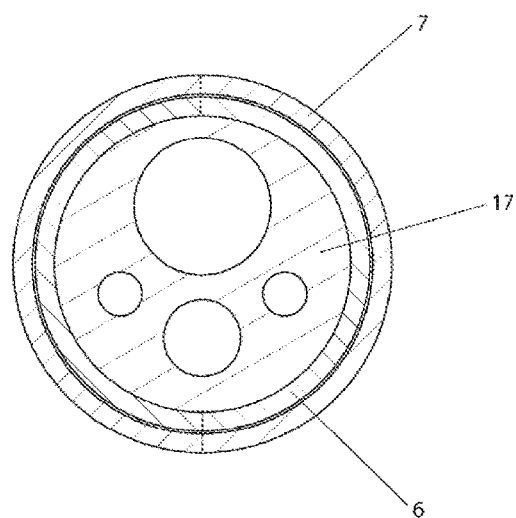
FIG. 10 is a drawing depicting an exemplary configuration of internal endoscope working channels of an endoscope end.

[FIG. 10] The material thickness of the inner sheath 6 and outer sheath 7 and overall cross-sectional diameter of the combined sheath assembly 2 must be minimal to allow ease of access into patient.

The sheath assembly 2, as described above, could be comprised of a single expanding layer 7 fitted directly onto the endoscope such that the endoscope acts as the internal bearing surface for accessory device introduction.

[FIG. 6] The joining seam 29 between the two layers of the sheath assembly 2 should be aligned to the fixing position 12 between the fixed 3 and rotating portions 4 of the apparatus assembly 1 such that the feed points will remain in the working portions of the sheath assembly 2 and not be obstructed by the joining seam 29.

Figure 11:
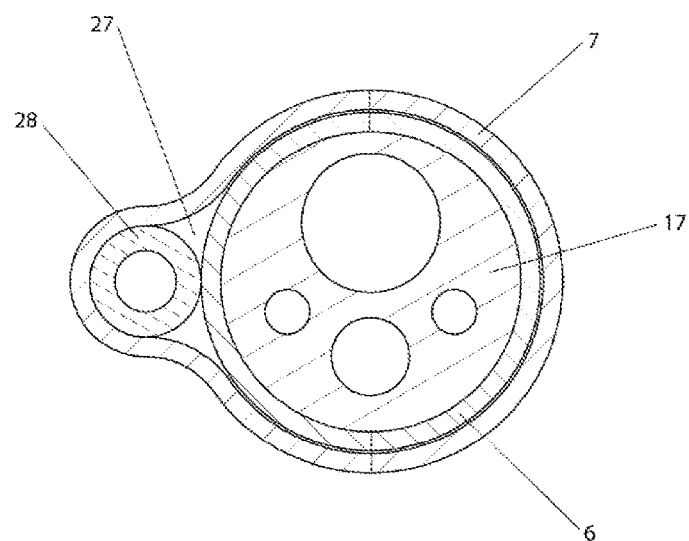
FIG. 11 is a drawing depicting the exemplary configuration of internal endoscope working channels of an endoscope end with an accessory.

[FIG. 8 & 11] In use, secondary accessories 28 are fed down through the access port 14, through the access funnel 15, into the gap between the inner sheath 6 and outer sheath 7 sheath in the sheath assembly 2. A working channel 27 is formed in the sheath assembly 2 as the outer sheath 7 expands to surround the accessory 28 being introduced. This continues down the length of the sheath assembly 2 as the accessory 28 is fed down, until said accessory 28 exits at the distal end 18 and is exposed for use. This position corresponds to the viewing position on the endoscope allowing viewing for use.

Figure 12:
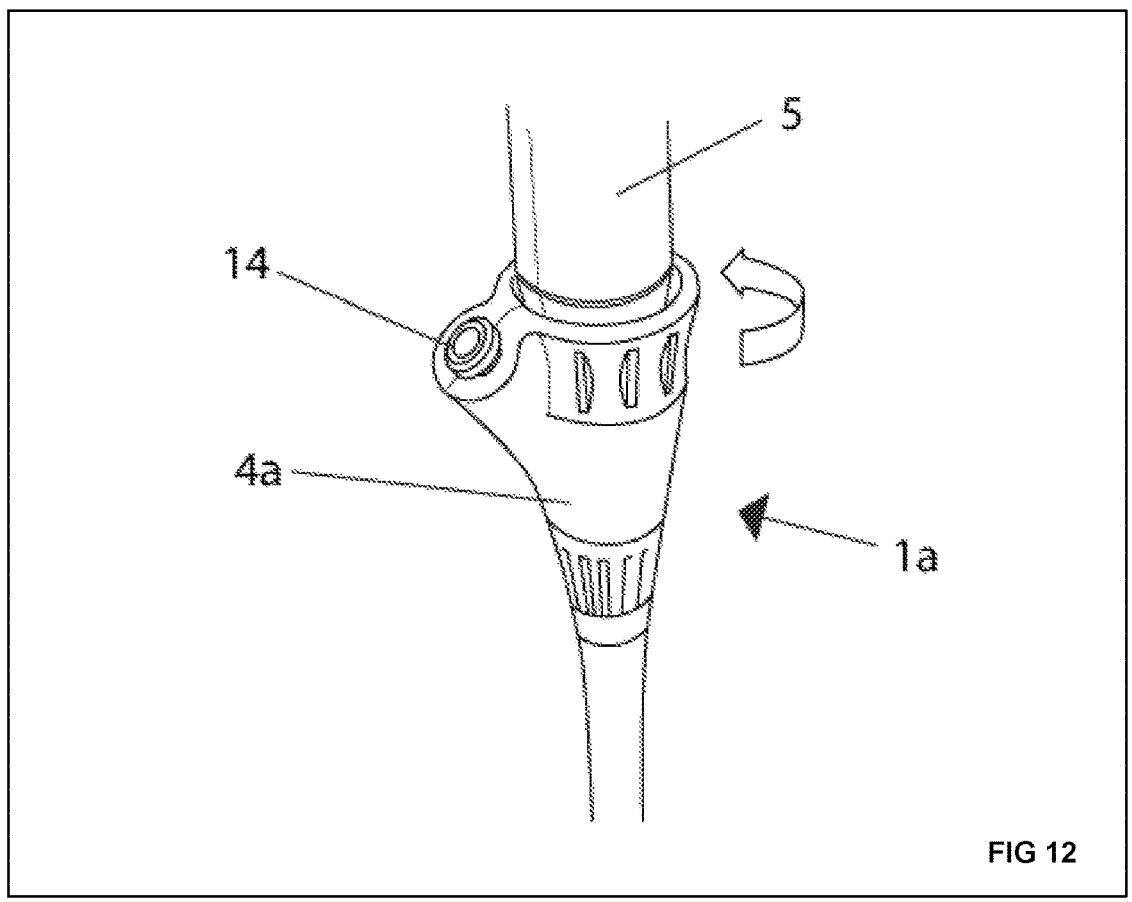
FIG. 12 is a drawing depicting another exemplary endoscope design in accordance with embodiments of the present invention, with a single access port for accessory entry.

[FIG. 12] An alternate embodiment is as described previously, but where the apparatus 1a, is comprised of a single access port 14 for accessory entry.

Figure 13:
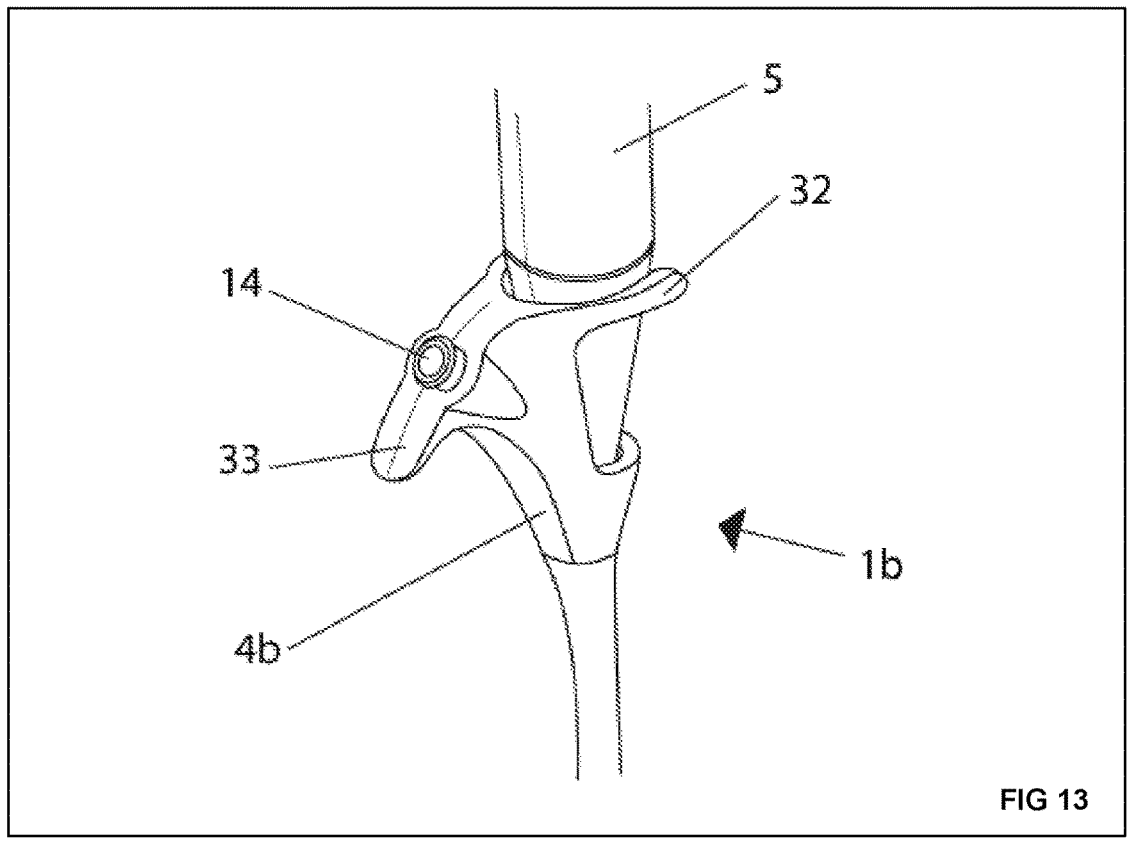
FIG. 13 is a drawing depicting another exemplary endoscope design in accordance with embodiments of the present invention, with an attachment apparatus.

[FIG. 13] An alternate embodiment for attaching the apparatus 1b to an endoscope 5 is the use of a flexible u-shaped clamp 32 that expands to surround and grip the endoscope 5. A pull tab 33 located on the apparatus 1b aids in positioning the apparatus 1b into position.

Figure 14:
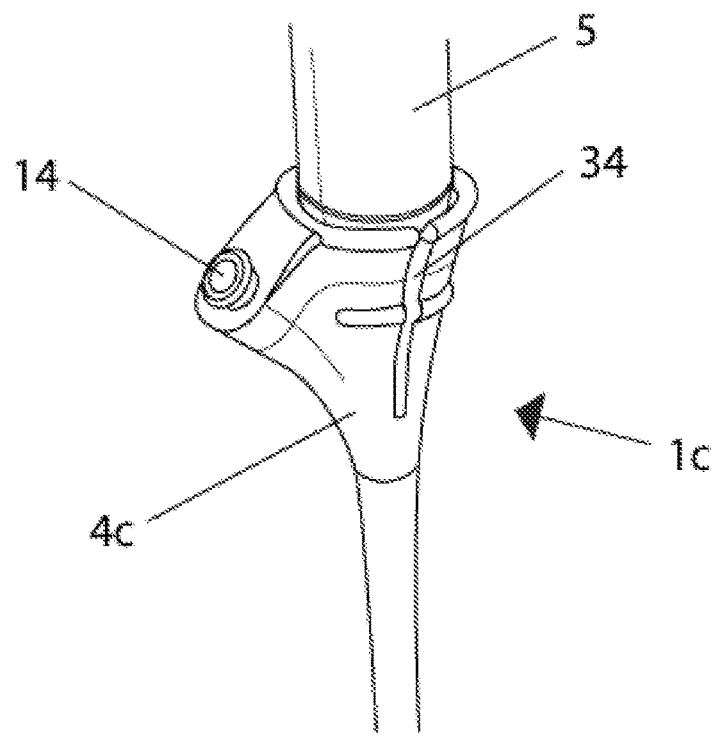
FIG. 14 is a drawing depicting another exemplary endoscope design in accordance with embodiments of the present invention, with gripping features.

[FIG. 14] Another embodiment is where the apparatus 1c incorporates features or textures internally to grip an endoscope 5 and where there is one or more splits 34 in the apparatus body 4c such that said body 4c can expand to fit a range of endoscope 5 diameters.

Figure 15:
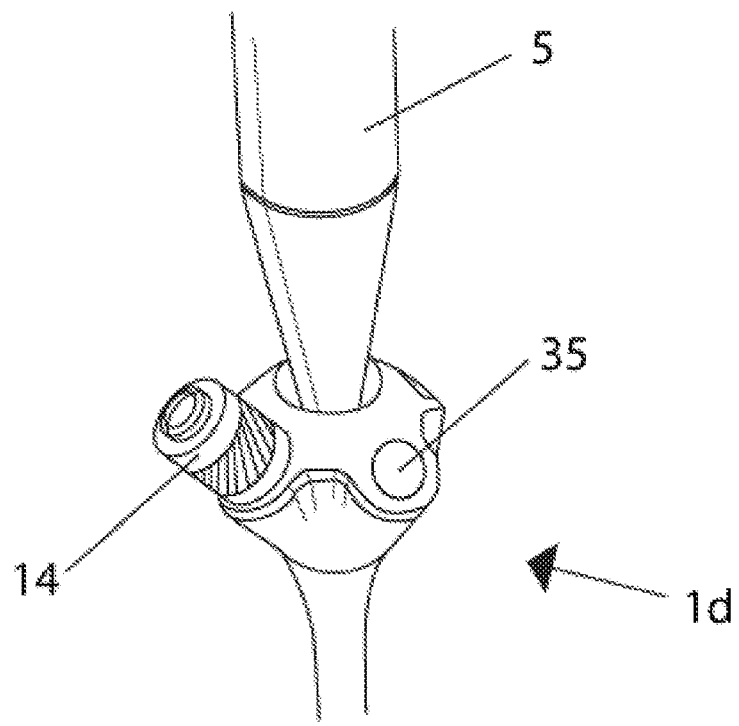
FIG. 15 is a drawing depicting another exemplary endoscope design in accordance with embodiments of the present invention, with multiple openings for access port fittings.

[FIG. 15] Another embodiment is for an apparatus 1d fixed to an endoscope 5 where said apparatus 1d is provided with a multitude of openings 35 such that a dedicated access port 14 can be fitted to same, thus providing a range of options for device positional delivery.

Figure 16:
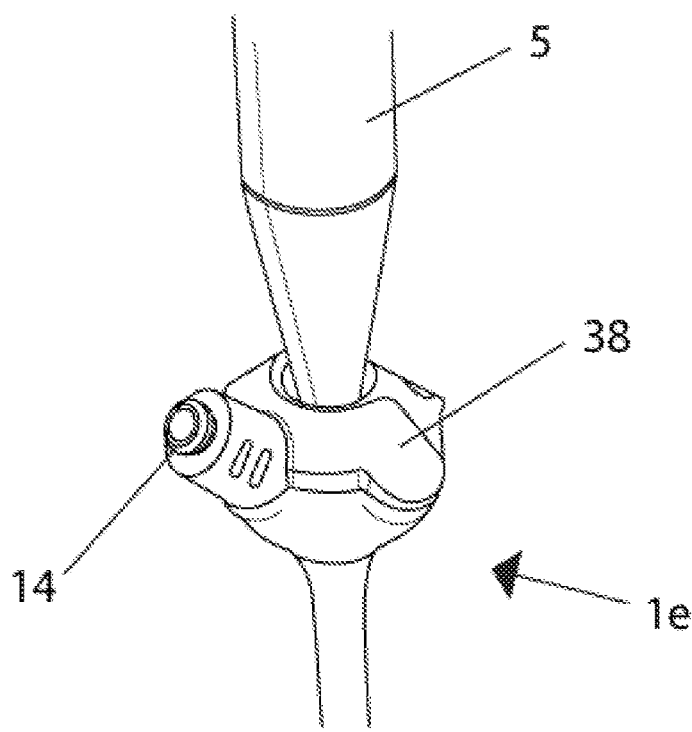
FIG. 16 is a drawing depicting another exemplary endoscope design in accordance with embodiments of the present invention, with an accessory cap for closing off access ports.

[FIG. 16] Another embodiment is for an apparatus 1e fixed to an endoscope 5 where said apparatus 1e is provided with a multitude of openings. An accessory cap 38 comprising an access port 14 is permitted to rotate between the said openings on the said fixed apparatus 1e.

Figure 17:
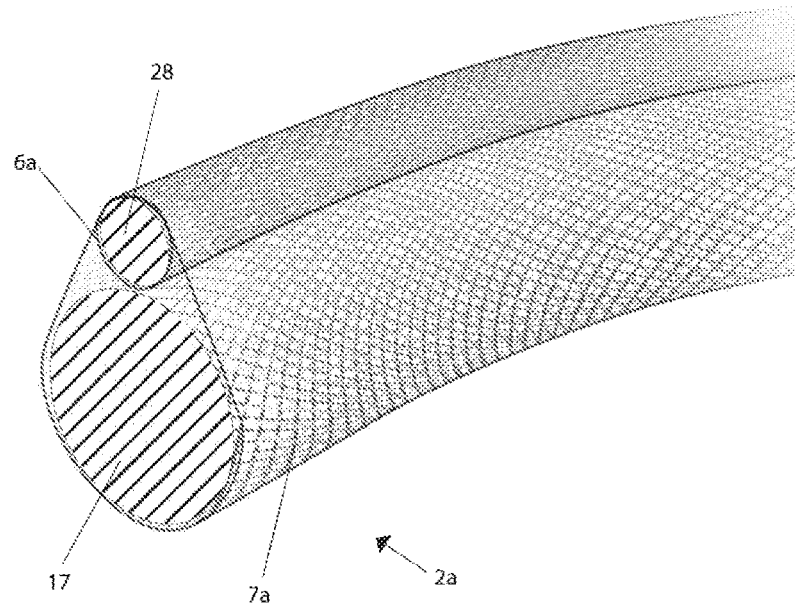
FIG. 17 is a drawing depicting an exemplary sheath assembly component of an endoscope.

[FIG. 17] Another embodiment for the sheath assembly 2a is where the inner sheath 6a does not fully surround the endoscope insertion tube 17 but is positioned between the outer sheath 7a and the endoscope insertion tube 17, providing a lumen for accessory 28 insertion. The inner sheath 6a is held in a flattened state prior to accessory 28 insertion, expanding to provide a channel when the accessory 28 is fed through. In this embodiment, said inner sheath 6a and said outer sheath 7a are manufactured from a braided mesh material to provide stretch.

Figure 18:
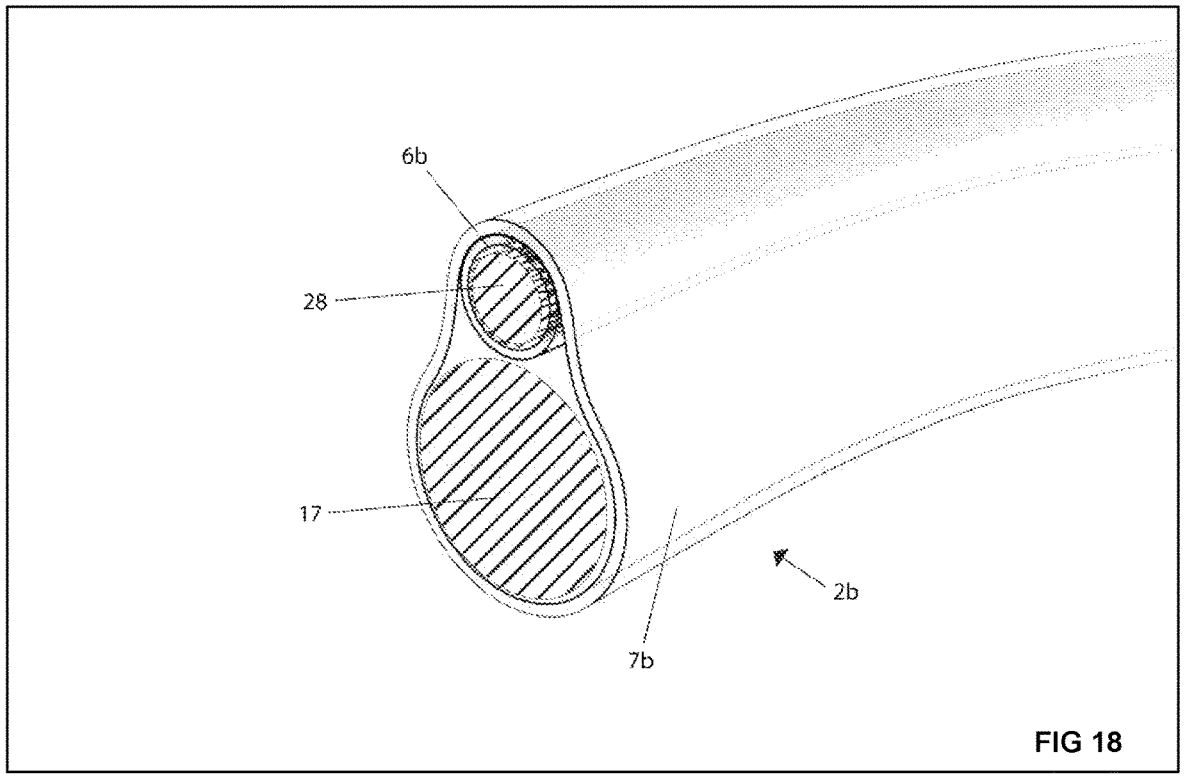
FIG. 18 is a drawing depicting another embodiment of an exemplary sheath assembly component of an endoscope.

[FIG. 18] Another embodiment for the sheath assembly 2b is where the inner sheath 6b does not fully surround the endoscope insertion tube 17 but is positioned between the outer sheath 7b and the endoscope insertion tube 17, providing a lumen for accessory 28 insertion. The inner sheath 6b is held in a flattened state prior to accessory 28 insertion, expanding to provide a channel when the accessory 28 is fed through. In this embodiment, said inner sheath 6a is manufactured from a braided mesh and said outer sheath 7a is manufactured in an elastic material.

Figure 19:
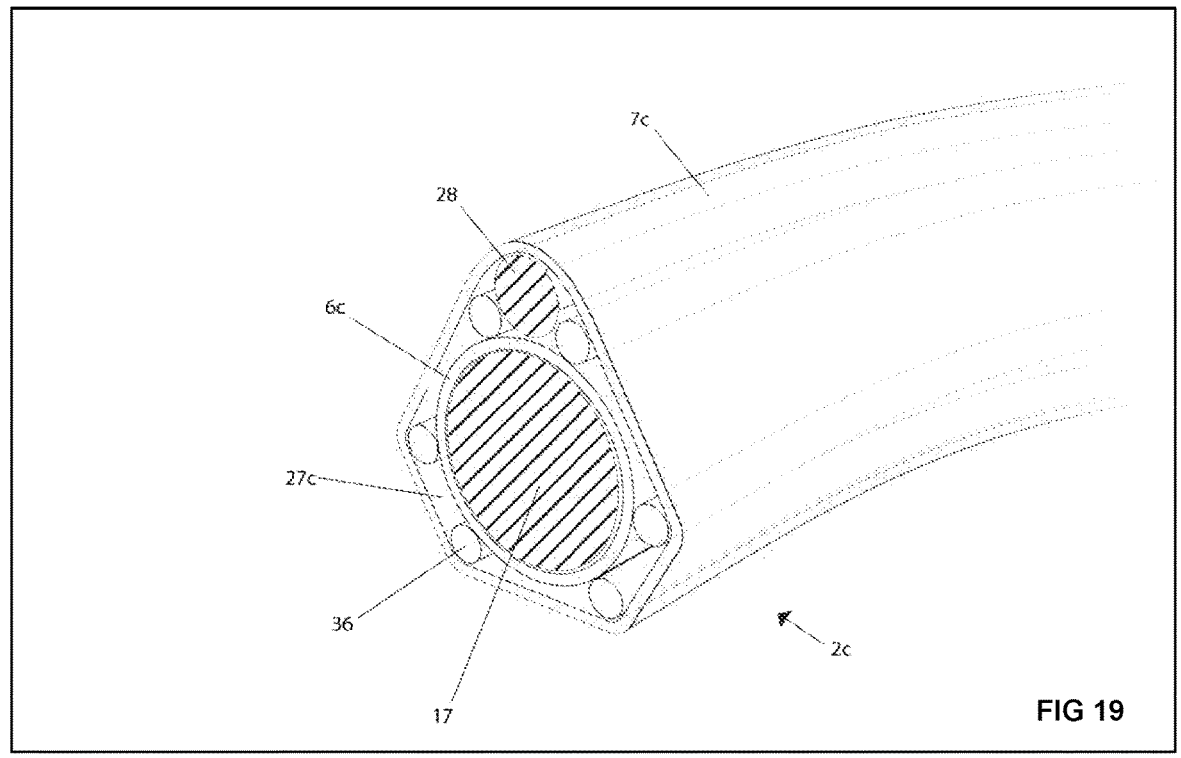
FIG. 19 is a drawing depicting another embodiment of an exemplary sheath assembly component of an endoscope, including plurality of channel-creating rods.

[FIG. 19] An alternate embodiment for the sheath assembly 2c is where there are a plurality of rods 36 positioned between the inner sheath 6c and an elastic outer sheath 7c, thus creating channels 27c between said rods 36.

Figure 20:
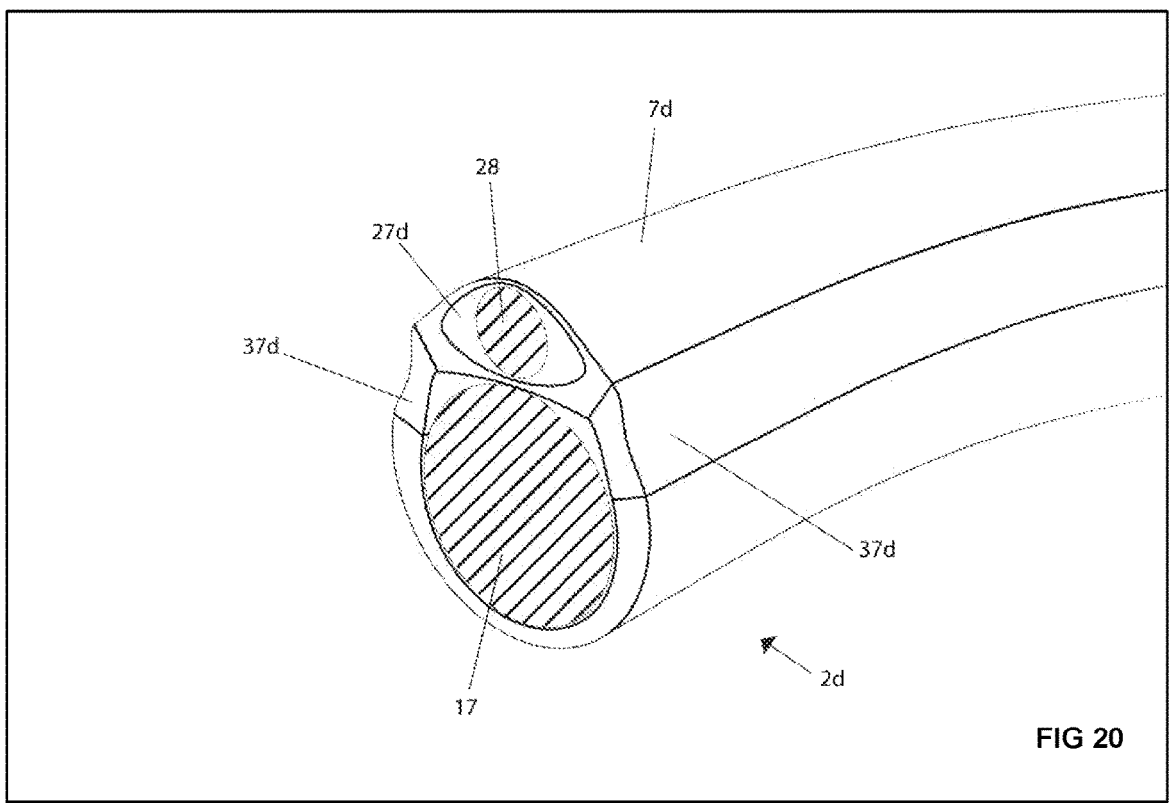
FIG. 20 is a drawing depicting another embodiment of an exemplary sheath assembly component of an endoscope, including a sheath formed of co-joined materials.

[FIG. 20] An alternate embodiment for the sheath assembly 2d is where said sheath assembly 2d is comprised of a single sheath 7d formed from two or more co-joined materials of differing properties such that there is a plurality of predominately non-elastic portions and a plurality of predominately elastic portions 37 running the length of said sheath. Said sheath 7d is of a specific thickness to permit the formation of a channel 27d in the part wall. Said channel 27d is held in a flat state prior to accessory 28 introduction.

When an accessory 28 is introduced the elastic portions 37 expand to open the channel 27d and permit the accessory 28 to pass through.

Figure 21:
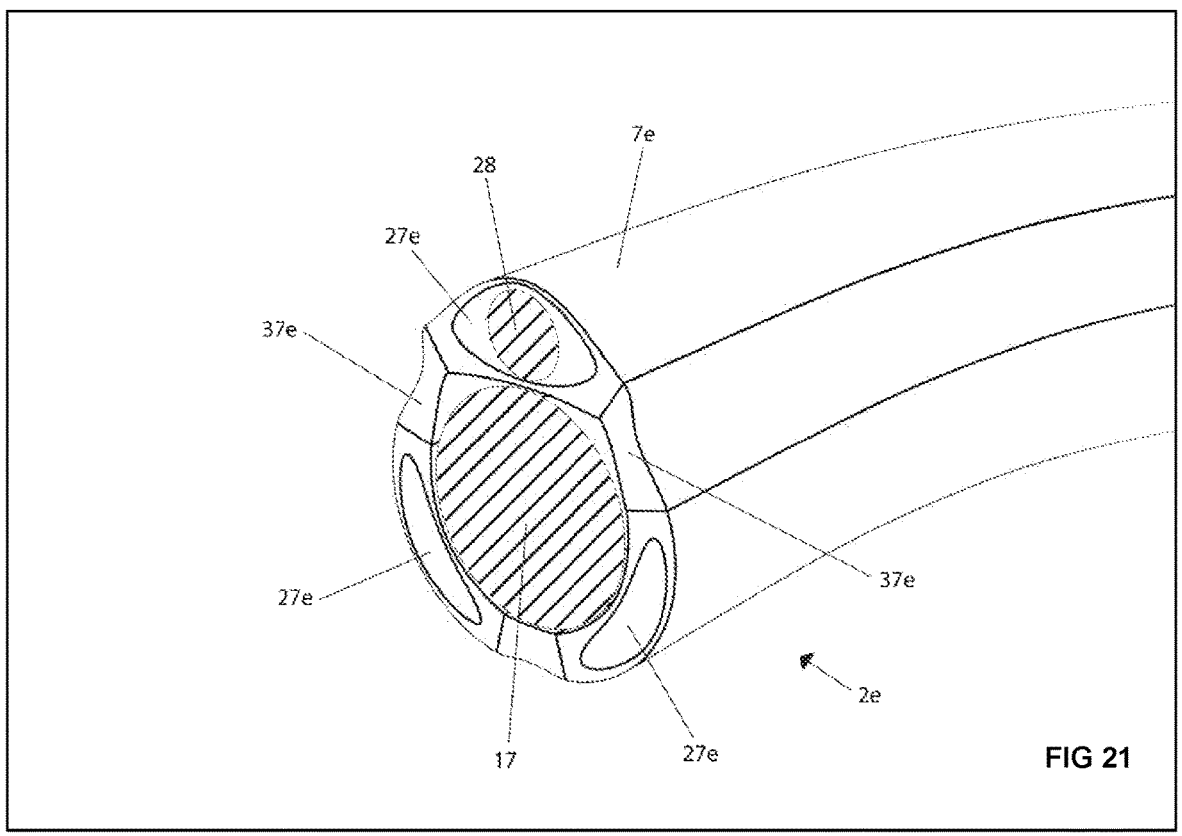
FIG. 21 is a drawing depicting another embodiment of an exemplary sheath assembly component of an endoscope, including a sheath formed of co-joined materials of differing properties.

[FIG. 21] An alternate embodiment for the sheath assembly 2e is where said sheath assembly 2e is comprised of a single sheath 7e formed from two or more co-joined materials of differing properties such that there is a plurality of predominately non-elastic portions and a plurality of predominately elastic portions 37e running the length of said sheath. Said sheath 7e is of a specific thickness to permit the formation of a plurality of channels 27e in the part wall. Said channels 27e are held in a flat state prior to accessory 28 introduction. When an accessory 28 is introduced the elastic portions 37e expand to open the channel and permit the accessory 28 to pass through.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. An accessory device introduction system which works in conjunction with an endoscope and enables more than one accessory device to be used at the same time, the accessory device introduction system has a plurality of channels which expand to accommodate accessory devices when introduced, the accessory device introduction system comprising:
    a. an attachment assembly comprising a fixed portion which connects securely to the endoscope by means of a compression friction fit between the endoscope and itself, and a rotating portion having a range of motion to rotate around a central axis of the fixed portion, the rotating portion comprising a plurality of accessory ports to be presented to an end user and a plurality of channels to enable the end user to pass an accessory device within said accessory ports and channels of the rotating portion of the attachment assembly; and
    b. a shaft sheath which is connected to the attachment assembly at one end and the distal end of the endoscope shaft at the other end therefore covering an entire outer shaft diameter length, the shaft sheath has a plurality of channels which correspond to the plurality of channels of the attachment assembly;
    wherein the rotating portion including the plurality of accessory ports and channels can be rotated independently of the fixed portion.

2. The accessory device introduction system according to claim 1, wherein the rotating portion including the plurality of accessory ports and channels can be rotated independently of the attachment to the endoscope.

3. The accessory device introduction system according to claim 2, wherein the rotating portion including the plurality of accessory ports and channels can be rotated independently of the attachment to the endoscope and within the channels of the shaft sheath.

4. The accessory device introduction system according to claim 1, wherein the rotating portion including the plurality of accessory ports and channels can be rotated independently of the attachment to the endoscope and between an inner and an outer sheath of the shaft sheath.

5. The accessory device introduction system according to claim 1, wherein the attachment assembly includes a universal griping feature configured to grip endoscopes of different diameters.

6. The accessory device introduction system of claim 1, wherein the shaft sheath has two tubular layers including an inner layer being flexible but not elastic, and an outer layer being elastic.

7. The accessory device introduction system according to claim 6, wherein the outer layer is elastic only in a radial sense, and the outer layer is not elastic co-axially along its length.

8. The accessory device introduction system according to claim 6, wherein the two tubular layers are fixated to each other coaxially along their length.

9. The accessory device introduction system according to claim 6, wherein the fixation of the two tubular layers coaxially along their length is stitched, glued, or heat treated.

10. The accessory device introduction system according to claim 6, wherein the inner tubular layer has a lubricous coating on its outer surface to aid the easy passing of accessory devices including wire guides.

11. The accessory device introduction system according to claim 10, wherein the outer tubular layer has a lubricous coating on its inner surface to aid the easy passing of accessory devices including wire guides.

12. The accessory device introduction system according to claim 6, wherein the inner tubular layer tapers relative to the outer tubular layer.

13. The accessory device introduction system according to claim 12, wherein the tapering of the inner tubular layer relative to the outer tubular layer accepts user controlled freely rotating accessory channels.

14. The accessory device introduction system according to claim 1, wherein the distal end of the endoscope shaft is left open so that the accessory channel in the endoscope can be used and a direct visualization camera is not obscured.

15. The accessory device introduction system according to claim 14, wherein the shaft sheath is designed so that it cannot be pulled over or pass the distal end of the endoscope.

16. The accessory device introduction system according to claim 14, wherein the distal end has exit openings which enable the accessory devices to exit in such a way so as to be visible under direct visualization.

17. The accessory device introduction system according to claim 6, wherein an outer surface of the outer tubular layer has a lubricous coating so as to aid the atraumatic passage within the human body, various coatings could be used including (but not limited to) Parylene, Teflon or bioresorbable elastomer made from polyglycerol sebacate.

18. The accessory device introduction system according to claim 7, wherein the outer tubular layer is a 2-way weft knit fabric, to allow for restricted or zero axial stretching and greater radial stretching.

* * * * *